United States Patent [19]

Dewhirst

[11] Patent Number: 4,786,669

[45] Date of Patent: Nov. 22, 1988

[54] LIGHTLY CROSS-LINKED RESIN MATERIALS

[75] Inventor: Kenneth C. Dewhirst, Houston, Tex.

[73] Assignee: Shell Oil Company, Houston, Tex.

[21] Appl. No.: 871,952

[22] Filed: Jun. 9, 1986

[51] Int. Cl.$^4$ .................. C08G 59/22; C08G 59/26
[52] U.S. Cl. ................... 523/445; 523/466; 523/468; 525/438; 528/97; 528/98; 528/94; 528/104; 528/27
[58] Field of Search ............ 528/97, 98, 99, 27, 528/104; 523/445, 466, 468; 525/438

[56] References Cited

U.S. PATENT DOCUMENTS

| | | | |
|---|---|---|---|
| 3,306,872 | 2/1967 | Maycock et al. | 260/32.8 |
| 3,410,825 | 11/1968 | Coover et al. | 528/97 |
| 3,419,624 | 12/1968 | Cotter et al. | 528/97 X |
| 3,546,165 | 12/1970 | Morgan | 260/47 |
| 3,635,843 | 1/1972 | Parry et al. | 528/97 |
| 3,637,590 | 1/1972 | Maycock et al. | 260/47 EP |
| 3,725,341 | 4/1973 | Rogers et al. | 528/97 X |
| 3,795,658 | 3/1974 | Thompson et al. | 528/97 |
| 3,821,162 | 6/1973 | Dexter | 260/45.8 N |
| 4,394,497 | 7/1983 | Nelson et al. | 528/97 X |
| 4,647,648 | 3/1987 | Silvis et al. | 528/102 |

FOREIGN PATENT DOCUMENTS 2142579 9/1972 Fed. Rep. of Germany.

OTHER PUBLICATIONS

J. F. McGrath, 29th National SAMPE Synposium, Apr. 3-5, 1984, pp. 447-458.

Primary Examiner—Earl Nielsen
Attorney, Agent, or Firm—Dean F. Vance

[57] ABSTRACT

The present invention relates to a new polymer composition having the processing characteristics of a thermosetting polymer along with an improved balance of properties including improved modulus/glass transition temperature/toughness balance. These new polymer compositions are prepared by reacting certain diphenolic compounds with certain diepoxide compounds to form linear units which are lightly crosslinked through the resulting secondary hydroxyl groups. Also disclosed and claimed are processes for preparing such compositions, cured compositions and end-use applications.

29 Claims, No Drawings

LIGHTLY CROSS-LINKED RESIN MATERIALS

FIELD OF THE INVENTION

The present invention relates to novel and unobvious polymer compositions which may be fabricated into thermoset composite structures by typical thermosetting resin methods. In particular, the present invention relates to compositions prepared by reacting a polyepoxide with a polyphenol to form linear molecules and lightly crosslinking the resulting linear molecules.

BACKGROUND OF THE INVENTION

Epoxy compositions and their curing techniques are well known, and the patents issued on curable epoxy compositions number in the hundreds. It will be appreciated that each and every one of the known epoxy-curing systems exhibits advantages over other systems, and, as importantlyj, disadvantages over the same system. There is, of course, a continuing need to develop better epoxy compositions.

There is, in particular, an increasing need in the automotive sector for high performance thermosetting compositions of matrices for fiber reinforced composites. Fiber reinforced composites are very desirable in automotive applications because they can offer a combination of good stiffness, strength and are light weight. Increasingly, the automotive manufacturers have demanded higher performance from the thermoset resins used in fiber reinforced composites. These higher performance thermoset resins are expected to possess these following characteristics:
good mechanical properties at temperatures up to about 90° C.
good thermal oxidative stability
good toughness properties, including good impact resistance
good fatigue properties
good chemical and solvent resistance
good fire resistance
high resistance to humidity, e.g., the "hot-wet" properties of the composite must remain high.

A further, and very important property of such systems is that the composite must have acceptable processing characteristics. For example, the current technique for manufacturing certain automotive components typically involves the use of liquid processes such as resin transfer molding (RTM). Therefore, the most desirable thermosetting resin compositions should be processable on the standard equipment currently utilized in the automotive industry.

A broad spectrum of thermosetting epoxy resin systems is currently being used by the automotive industry, primarily as composite matrices and adhesives. As a class, epoxy resin systems are very versatile materials offering, as mentioned above, chemical resistance, high adhesive strength, good electric properties and are easy to use or process into composites. However, to improve their high temperature properties, such current epoxy resin systems must be highly crosslinked. This crosslinking, however, results in generally lower toughness.

One good resin system possessing improved impact is based on Shell Chemical Company EPONOL ® Resins. These thermoplastic polyethers are disclosed and claimed in U.S. Pat. No. 3,637,590, while the process for preparing such polymers is claimed in U.S. Pat. No. 3,306,872. Even though such polymers, which are based on the reaction product of certain diepoxides with certain bisphenols, have improved impact strength, such polymers lack adequate high temperature properties and solvent resistance for high performance applications. Similar compositions having improved impact strength are also disclosed in Fed. Rep. of Germany OLS No. 2,142,579 where certain diepoxides are reacted with certain diphenols (e.g., 2,2-bis(4-hydroxynaphth-1-yl)propane) to produce polymers for eyeglasses.

SUMMARY OF THE INVENTION

The present invention relates to a polymer composition having the processing characteristics of a thermosetting polymer along with an improved balance of properties including improved modulus/glass transition temperature/toughness balance. In particular the present invention relates to a polymer composition comprising lightly crosslinked linear molecules having the repeating structures prior to crosslinking of the general formula:

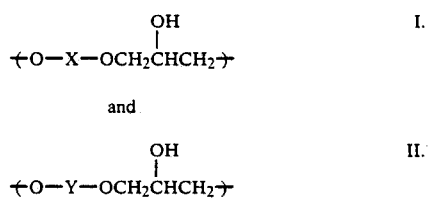

where:
(a) "X" represents a stiff segment comprising stiff units (SU) and optional flexible units (FU), which stiff units and flexible units are interconnected;
(b) "Y" represents a flexible segment comprising stiff units (SU') and optional flexible units (FU') which stiff units and flexible units are interconnected;
(c) said stiff units, SU and SU', are independently selected from the group consisting of substituted and non-substituted aromatic rings, cycloaliphatic rings and heterocyclic rings;
(d) said flexible units, FU and FU', are independently selected from the group consisting of $$-\overset{|}{\underset{|}{C}}-, \quad \overset{|}{\underset{/\,\backslash}{N}}, \quad \underset{/\,\backslash}{O}, \quad -\overset{|}{\underset{|}{Si}}-, \quad \underset{/\,\backslash}{\overset{|}{B}} \text{ and } \underset{/\,\backslash}{S};$$

(e) the number of stiff segments in said molecules is "a", the number of flexible segments in said molecules is "b", and the ratio of $$\frac{a}{a+b}$$

is between zero and one;
(f) the number of stiff units and flexible units are selected such that the average number of total stiff units

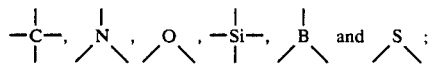

divided by the average number of total flexible units

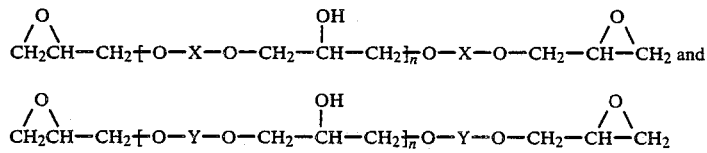

is less than or equal to four and;

(g) the ratio of the number of stiff units to flexible units in said stiff segment (SU/FU) is equal to or greater than the ratio of the number of stiff units to flexible units in said flexible segment (SU'/FU');

In another embodiment, this invention relates to a process for preparing such thermoplastic polymers (prior to crosslinking), said process comprising reacting:

(a) a first component selected from the group consisting of phenol compounds of the formula HO—X—OH or HO—Y—OH, where X and Y represents the stiff segment and flexible segment respectively, defined above; with (b) a second component, said second component being a diepoxide selected from the group consisting of $$\overset{O}{\underset{CH_2CH-CH_2}{\diagup\diagdown}}\!\!\!\!\!\!+O-X-O-CH_2-\underset{OH}{\underset{|}{CH}}-CH_2\!\!\!\!\!\!\frac{}{}]_n O-X-O-CH_2-\overset{O}{\underset{CH-CH_2}{\diagup\diagdown}} \text{ and} \qquad \text{III.}$$

$$\overset{O}{\underset{CH_2CH-CH_2}{\diagup\diagdown}}\!\!\!\!\!\!+O-Y-O-CH_2-\underset{OH}{\underset{|}{CH}}-CH_2\!\!\!\!\!\!\frac{}{}]_n O-Y-O-CH_2-\overset{O}{\underset{CH-CH_2}{\diagup\diagdown}} \qquad \text{IV.}$$

and (c) a catalytic amount, not in excess of 0.1 mole per mole of said first component, of a basic condensation catalyst at a temperature of about 130° to about 230° C. for about 1 to about 24 hours and with a molar ratio of phenol compounds to diepoxides of about 0.90:1 to about 1.04:1 until the desired linear reaction product has been formed, and thereafter stopping the reaction.

Also disclosed and claimed herein are compositions containing fibrous reinforcing materials, prepregs prepared from such reinforced compositions and articles prepared form such prepregs.

ADVANTAGES AND OBJECTS OF THE PRESENT INVENTION

One object of the present invention is to tailor make polymers for particular applications, i.e., to design polymers having the required balance of solvent resistance, thermal properties, mechanical properties and toughness for the specific application end use.

Another object of the present invention is to prepare fiber reinforced composites having particular utility in automotive applications.

Still other objects and advantages will be apparent from the application.

As shown in the examples which follow, applicant has discovered a new method for preparing novel polymers wherein it is now possible to obtain both good temperature performance and high toughness, i.e., applicant has discovered a means to uncouple the usual temperature/toughness balance relationship. In particular, in a preferred embodiment applicant has prepared polymers having the following property set:

Glass transition temperature, $T_g = 121°$ C. (DSC)
Fracture toughness, $K_q = 2.4$ $KSI\sqrt{in}$ (Compact Tension)
Flex modulus, $E = 370$ KSI (Dry @ R.T.)
Impact Strength = 4.8 ft.lb/in
Water gain, $\alpha W/W_0 = 2.5\%$ (saturation)

The present patent application is related to my copending application, Ser. No. 871,951, which covers higher performance materials.

DETAILED DESCRIPTION OF THE INVENTION

There are two basic aspects to the present invention—one involves the process for making certain thermoplastic polymers and the other involves the polymers as compositions-of-matter.

I. Process

Part of the present invention relates to preparing a mixture of a diphenol component and a diepoxide component to make a prepolymer composition, which may be stored for later reaction or which may be reacted with a condensation catalyst.

A. diphenol Component

In a preferred embodiment the diphenol components employed herein have the structure HO—X—OH or HO—Y—OH where "X" represents the stiff segment specified above and "Y" represents the flexible segment specified above.

As a practical matter, it is preferred that the diphenol component contain the stiff segment, i.e. that the phenol component be HO—X—OH. The reason for this is that it is easier to synthesize the diphenol component (containing the relatively large number of stiff units) than it is to glycidate the corresponding diphenol compound. In particular, it is preferred to employ diepoxides based on BPA and use diphenol compounds based on the less common compounds. However, in certain cases it may be preferable to have the stiff segment, X, in the diepoxide component since the diepoxide may have a lower melting point than the diphenol component, resulting in an easier thermoplastic polymer synthesis, especially if it is desired to perform the synthesis in the melt as opposed to a solution preparation.

Preferably it is desired that the diphenol compound be meta or para derivatives as opposed to an ortho structure.

An important aspect of the present invention is the selection of stiff units and flexible units such that the resulting polymer molecules have the appropriate type and ratio of stiff units to flexible units.

By use of the term "flexible units" are meant those units that permit rotation at an angle. Examples of such flexible units are Broad group         Examples

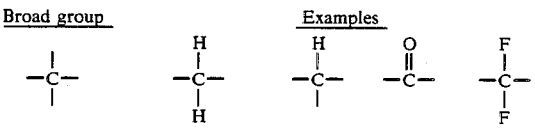

| Broad group | Examples |
|---|---|
|  |  |
|  | 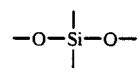 |
|  | |
|  |  |

The stiff units are selected from the group consisting of substituted or non-substituted aromatic rings, cycloaliphatic rings and heterocyclic rings. The aromatic rings are inertly substituted or un-substituted benzene radicals. Substituted benzene radicals have substituents which do not interfere in the process independently selected from the group consisting of Cl, Br or $C_1$–$C_5$ alkyl groups. Annulation of benzene rings gives rise to

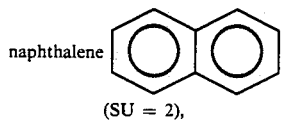

naphthalene (SU = 2),

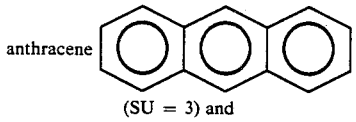

anthracene (SU = 3) and

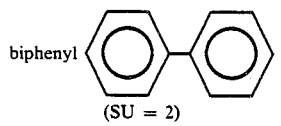

biphenyl (SU = 2)

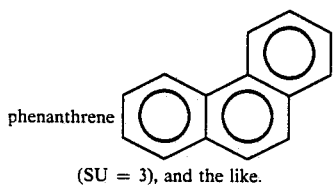

phenanthrene (SU = 3), and the like.

The cycloaliphatic rings are substituted or un-substituted $C_5$ or $C_6$ hydrocarbon radicals. Substituted cycloaliphatic rings are analogous to substituted aromatic rings. Un-substituted rings include, by way of example, cyclopentane, cyclohexane and cyclohexene. Annulation of cycloaliphatic rings gives rise to

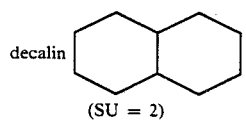

decalin (SU = 2)

[2.2.2]bicyclotane (SU = 3)

norborane (SU = 3)

adamantane ($C_{10}H_{16}$)

(SU = 4) and the like.

The term heterocyclic rings refers to substituted or un-substituted 5–6 membered heterocyclic radicals. Examples of 5–6 membered heterocyclic radicals are radicals of

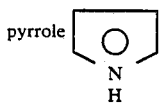 pyrrole    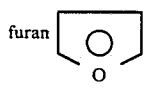 furan

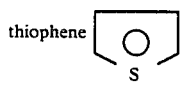 thiophene    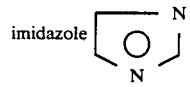 imidazole

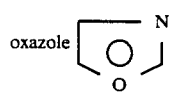 oxazole    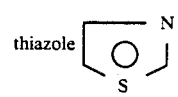 thiazole and

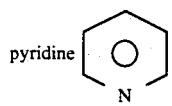 pyridine

Annulation of heterocyclic rings with aromatic rings give rise to

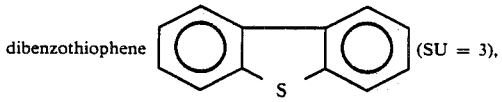

dibenzothiophene (SU = 3),

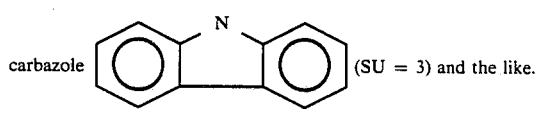

carbazole (SU = 3) and the like.

Regarding the selection of heterocyclic structures, O and S heterocycles are generally suitable. In the case of N derivatives, however, care must be exercised such that the N is not strongly basic so that homopolymerization of the epoxide occurs. For example,

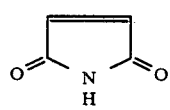

is suitable, but

may not be suitable by itself (however the carbazole analog is suitable since the N is not strongly basic there).

One group of diphenol components useful herein are those mentioned in U.S. Pat. No. 3,546,165. Specifically, those useful components are those phenoxy compounds of the formula

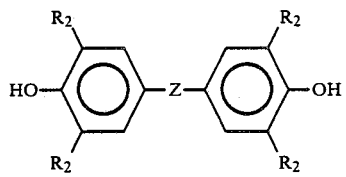

where each $R_2$ substituent is independently selected from H, Cl, Br or $C_1$-$C_5$ alkyl and Z is a substituent having flexible units (FU or FU') and stiff units (SU or SU') where Z represents a gem-bivalent radical having 1 to 2 aromatic hydrocarbon rings and a gem-bivalent non-aromatic ring selected from the group consisting of a ring of 5 carbon atoms, a ring of 6 carbon atoms one of which carbon atoms may bear an oxo oxygen atom, and a ring of 5 carbon atoms and one oxygen atom, said gem-bivalent non-aromatic ring being fused to said aromatic hydrocarbon rings. Also useful are those components where Z is

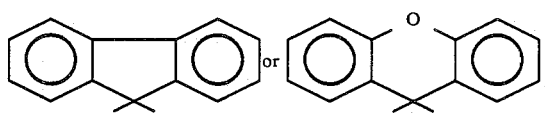

Specific examples include the following bisphenols:
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone,
9,9-bis(4-hydroxyphenyl)phenanthrone.

Other useful bisphenols include phenolphthalene,
9,9-bis(4-hydroxyphenyl)-9,10-dihydroanthracene,
9,9-bis(4-hydroxyphenyl)-10,10-diphenyl-9,10-dihydroanthracene,
3,3-bis(4-hydroxyphenyl)-4,5-benzodihydrofuran, and the like.

Another group of diphenol components useful herein are the imides represented by the formula

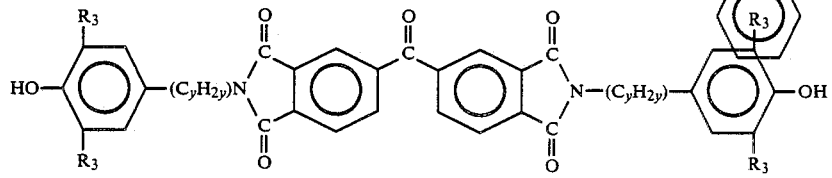

wherein each of $R_3$ is the same or different (lower) alkyl group of from one ot four carbon atoms; and y has a value of from 0 to 3. Such diphenol compounds are disclosed in U.S. Pat. No. 3,821,162 and reported by J. E. McGrath, 29th National SAMPE Symposium, Apr. 3-5, 1984, page 447.

Still another group of diphenol compounds are those based on phthalocyanine. Such compounds include the following:

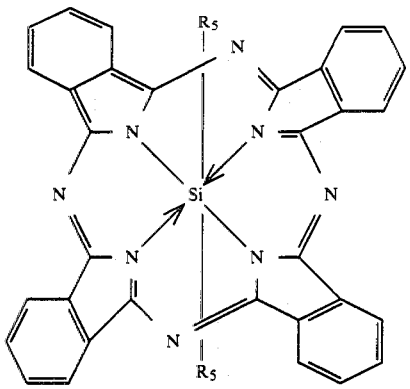

(a) $R_5$ = OH

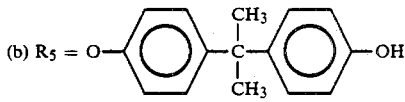

(b) $R_5$ =

Still another group of diphenol compounds are those shown below. Additional aromatic, cycloaliphatic or heterocyclic rings may be annulated as desired:

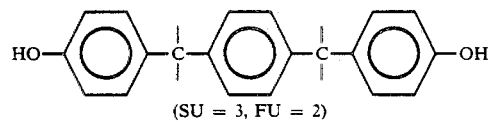

(SU = 3, FU = 2)

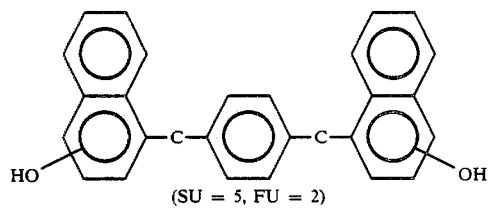

(SU = 5, FU = 2)

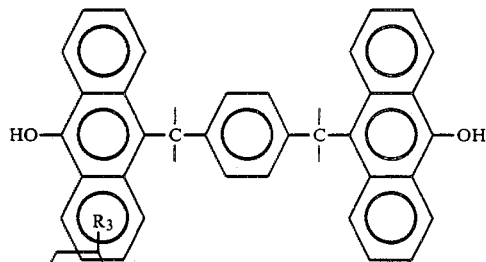

-continued
(SU = 7, FU = 2)

This particular group of diphenol compounds are distinguished from diphenol compounds such as BPA and the like, by the presence of 2 or more flexible units

Preferably the diphenoxy compounds used herein are represented by the general formula

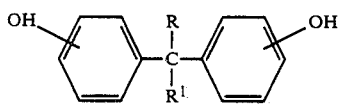

in which R and $R^1$ when taken collectively with the connector carbon C are selected from the group consisting of cyclohexyl and alkyl-substituted cyclohexyl, and when taken separately are from the group consisting of hydrogen, alkyl, cyclohexyl, phenyl, alkyl-substituted cyclohexyl, alkyl substituted phenyl, halogen substituted cyclohexyl and halogen substituted phenyl groups with the total number of carbon atoms in the group or groups attached to said connector carbon atom not exceeding eighteen and the number of carbon atoms in any of said alkyl substituent groups not exceeding six. The preferred phenols have the hydroxyl groups in the 4,4'positions, but compounds with hydroxyls in the 2,2', 3,3', 2,4', and other arrangements may also be used. R and $R^1$ suitable are methyl, ethyl, isobutyl, n-nonyl, n-heptadecyl and the like. Other dihydric phenols may also be employed, excepting those which have two hydroxyl groups in ortho positions on a single benzene ring.

The dihydric phenol employed in the process of this invention may be substantially 100 percent pure, or may be a technical grade of somewhat lower purity. Concentrates of dihydric phenols containing, for example, 90 to 100 percent of the pure compound may be used.

B. Diepoxide Component

The second reactant in the condensation process, the diepoxide, is a compound having two vicinal epoxide groups (oxirane rings) in terminal (or optionally nonterminal) positions in the molecule, usually in the form of an oxygen atom bound to two terminal carbons of an alkyl group, though the epoxide may also be one a ring, such as a cyclohexyl ring. Suitable diepoxides are terminal diepoxyalkanes, e.g., 1,2-epoxy-3,4-epoxybutane, 1,2-epoxy-5,6-epoxyhexane, 1,2-epoxy-7,8-epoxyoctane and the like. Others are terminal diepoxides containing either linkages, such as bis(2,3-epoxypropyl)ether and bis(2,3-epoxy-2-methylpropyl)ether; diglycidyl ethers of alpha, omega glycols such as the diglycidyl ethers of ethylene glycol, trimethylene glycol, and tetramethylene glycol; and diglycidyl ethers of dihydric phenols.

Diglycidyl ethers of the dihydric phenols referred to above are generally suitable for use in this invention. One may suitably use the diglycidyl ether of the same phenol which is employed as the other reactant. Thus, for example, bisphenol acetone (BPA) is suitably condensed with diglycidyl ether of bisphenol acetone. Useful resins can also be prepared by condensing a dihydric phenol with the diglycidyl ether of a different dihydric phenol.

In preparing the products of this invention the epoxy reagent may be a pure diepoxide or a crude mixture containing a substantial proportion of diepoxide, e.g., 70% or more. It is important, however, that the crude reagent is free of monoepoxide and of monohydric alcohol or phenol. The polyepoxides used herein have the structure III or IV, as shown in the Summary of Invention. The number "n" has a value of 0 to about 6, preferably 0 to about 2, more preferably zero.

A particularly preferred diepoxide is the diepoxide is the diglycidyl ether of BPA. Such diepoxides are available from Shell Chemical Company as EPON ® Resins 825 and 828. Shell EPON Resin 825 is an essentially pure diepoxide of BPA (where n=0) while EPON Resin 828 is a diepoxide of BPA having a slightly higher average molecular weight and containing a small amount of n=1.

C. Selection of Stiff Units and Flexible Units for Stiff Segments and Flexible Segments A key aspect of the present invention is the selection and location of the stiff units (SU and SU') and flexible units (FU and FU') for the stiff segments (X) and flexible segments (Y). As discussed above, the stiff segment (X) may be located in either the diphenoxy component or diepoxide component or in both components. For ease of synthesis it is preferred that the stiff segment be in either the diepoxide component or the diphenoxy component. The selection will depend upon the particular components to be employed. For example, since the diepoxide of BPA is readily available, it may be preferable to use such a polymer in the synthesis. Since the diepoxide of BPA has one flexible unit and two stiff units, it has an $$\frac{FU'}{SU'} \text{ of } \frac{2}{1}$$

or 2. Then one must use a diphenol component having sufficient number of stiff units (SU) and flexible units (FU) such that the ratio $$\frac{\frac{a}{a+b} \cdot SU + \frac{b}{a+b} \cdot 2}{\frac{a}{a+b} \cdot FU + \frac{b}{a+b} \cdot 1}$$

is less than or equal to 4. Where $$\frac{a}{a+b}$$

is 0.5 then $$\frac{0.5 \, IU + 1}{0.5 \, SU + .5} \leq 4$$

and therefore SU=4FU=2. For example, the bisphenol of acetone (BPA) has two stiff units and one flexible unit. Accordingly, the reaction product of a 50:50 mixture of BPA and the diglycidyl ether of BPA has a ratio of $$\frac{SU}{FU} \text{ of } \frac{2}{1}$$

and a ratio of $\frac{SU}{FU}$ of $\frac{2}{1}$

The average of $$\frac{\frac{a}{a+b}SU + \frac{b}{a+b}SU'}{\frac{a}{a+b}FU + \frac{b}{a+b}FU'}$$

is $$\frac{0.5 \times 2 + 0.5 \times 2}{0.5 \times 1 + 0.5 \times 1} = 2,$$

which is the average number of total stiff units divided by the average number of total flexible units.

More particulars on these ranges and selections are found in the discussion of the Structures of the Resulting Polymers.

D. Catalyst and Reaction Conditions

The condensation reaction between the diphenol component and the diepoxide component requires the presence of a condensation catalyst, typically a basic condensation catalyst. The catalyst may, for example, be added as a concentrated aqueous solution of sodium or potassium hydroxide or a sodium salt of a phenol. One may also use halides, carboxylates or other nucleophiles. It is sometimes desirable to use a catalyst a sodium salt of the same dihydric phenol which is used as a reactant. These salts are generally solids which are dissolved in the reaction mixture. It has been found that very satisfactory results are also obtained when using concentrated aqueous sodium hydroxide or benzyltrimethyl ammonium hydroxide. When the catalyst is added as an aqueous solution, a concentrated solution is used since it is not desirable to have more than a small amount of water present in the reaction mixture.

The concentration of catalyst present during the condensation reaction must be held to a low value; otherwise branched polymers of low impact value are produced. However, it has also been found that reaction rates increase proportionately with catalyst concentration. The useful range of catalyst concentration is from 0.0001 to 0.100 mole per mole of the contained bisphenol. For best results the concentration is preferably between 0.001 and 0.010 mole per mole. It may occur that some of the catalyst reacts with impurities in the reactants. This results in a reduction of the rate of reaction and can stop the reaction prematurely. Adding a further amount of catalyst then permits the reaction to continue. It has been found that basic catalyst reacts with saponifiable chlorine if the latter is present in the diglycidyl ether reactant. It is therefore useful to add initially an extra amount of catalyst, sufficient to react with such chlorine, to prevent slowing down of the reaction.

It is preferred to keep the water content of the reaction mixture as low as possible, preferably below 0.5% by weight, more preferably below 0.2% by weight, and still more preferably below 0.12% by weight. In any event, the water content is to be maintained so as not to exceed about 1 percent by weight.

Careful control of the ratio of dihydric phenol and diglycidyl ether in the reaction mixture is of greatest importance in order to obtain a product having the desired characteristics. When technical grades of one or several reagents are employed, the correct ratio is maintained by determining the epoxy equivalence and the phenolic hydroxide equivalency of the reagents and carrying out the reaction with a mixture which contains not less than 0.90 phenolic hydroxide group per epoxide group and not more than 1.04 phenolic hydroxide group per vic epoxide groups

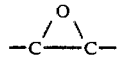

Best results are obtained with phenolic hydroxide/epoxy ratios in the range from 0.94 to 1.0 A slight excess of epoxy groups is preferred to a small excess of phenolic hydroxyl groups. When the catalyst employed is a basic salt of a dihydric phenol, then the phenol present in the catalyst is considered part of the phenolic reagent for purposes of calculating the proper ratio of reactants. Similarly, when the technical grade of the diepoxide contains some saponifiable chlorine, the chlorohydrin groups are considered the equivalent of epoxy groups since they are converted thereto during the condensation reaction in the presence of a basic catalyst. It is also desired to keep the saponifiable chlorine content low.

The reaction is typically carried out in solution in a solvent which meets the following criteria: (1) It is capable of maintaining reactants and reaction products in solution, at reaction temperatures, in the concentrations employed. These concentrations generally range between 20 and 60 percent by weight of the total reaction mixture. When the original concentration is high, it is generally necessary to add additional solvent during the course of the reaction to reduce the viscosity of the mixture and to maintain the product in solution. (2) It does not react significantly with epoxide groups or phenolic hydroxyl groups. Water and alcohols, for example, tend to interreact with the reactants and are therefore not suitable as solvents. (3) It is readily and completely removable from the final reaction mixture to permit recovery of a resin substantially completely free of solvent. Desired high impact resistance is a property which requires complete removal of solvent. In the production of resin for use in molding, extrusion, and the like, solvent is removed from the reaction mixture. In the production of resin for surface coatings, the resin may remain associated with solvent until it is actually applied as a coating and the solvent is removed by evaporation under suitable conditions. (4) Its boiling point must be such that the reaction can be carried out at 75° to 150° C. at a practical pressure. The solvent may be a mixture of individual compounds.

Useful solvents which meet those criteria are, for example, certain ketones, halogenated hydrocarbons and ethers. Methyl ethyl ketone is a preferred solvent. Cyclohexanone, methyl isobutyl ketone and the other ketones may be used. Chloroform, 1,2-dichloroethane and other chlorinated hydrocarbons may be used, particularly in admixture with ketones. Ethers, such as dioxane, tetrahydrofuran, dimethoxyethane and lower alkyl (methyl or ethyl) ethers of ethylene glycol are suitable, alone or in admixture with ketones. Other solvents which meet the above criteria may be employed if desired, such as N-methyl pyrrolidone.

While in the examples which follow the synthesis was performed in solution, it is also possible (and desirable in some cases) to do the synthesis in the absence of solvent, i.e. as a melt. In such cases it may be desirable to use the diepoxide containing the stiff segment since the melting point of diepoxide component is usually much lower than the melting point of the corresponding diphenoxy component.

A necessary process step for obtaining solid resin of high impact resistance suitable for molding or other forming is the complete removal of solvent from the resin mass.

II. Resulting Polymers

A. Structures

As mentioned above, a key aspect of the present invention is the selection and location of the stiff units (SU and SU') and the flexible units (FU and FU') for the stiff segments (X) and flexible segments (Y). Great latitude is provided for the selection and location of the particular components. For most part the properties and performance of the resulting polymers depend primarily on the relative number of stiff units and flexible units (*each* such *unit* being assigned a value of *one*). However, there are certain important ratios and values that need to be followed.

Note that it is not necessary that the segments contain flexible units. For example,

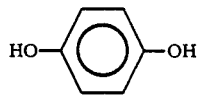

does not contain flexible units and is perfectly satisfactory.

The first important ratio is the average number of total stiff units divided by the average number of total flexible units. This ratio must satisfy the equation:

$$\frac{\frac{a}{a+b}SU + \frac{b}{a+b}SU'}{\frac{a}{a+b}FU + \frac{b}{a+b}FU'} \leq 4$$

Preferably this ratio is greater than 1.5 and less than 4. More preferably this ratio is about 2. This ratio is important because it is an important factor in determining the Tg, or heat resistance of the polymer.

The second important ratio is that SU/FU must be equal to or greater than SU'/FU', preferably greater. In other words, the stiff segment (X) must have an equal or higher ratio of SU/FU than the flexible segment (Y) ratio of SU'/FU'. This is important because it helps determine the Tg/toughness balance. Preferably SU/- FU>SU'/FU'+0.5. In a preferred embodiment SU'/FU' is between 1 and 4, preferably between 2 and 3. For example, where it is preferred to use the diglycidyl ether of BPA, the SU'/FU' ratio is 2/1 or 2.

B. Light Crosslinking

Another important aspect of the present invention relates to the light crosslinking of the thermoplastic polymer molecules to form the resulting polymer matrix. The concept and process for light crosslinking of such polymers is another novel and unobvious aspect of the present invention. In the broadest sense, light crosslinking refers to the crosslinking of between 1 and 50 out of each 100 repeat units of other molecules, e.g. formulas I or II of said thermoplastic polymer. Preferably, the crosslinking density is between 2 and 20 out of 100, more preferably between about 3 and 10 repeat units per 100 repeat units.

"Light crosslinking" is distinguished from the normal crosslinking or curing of epoxy resins where the crosslink density approaches 100 (stoichiometric) molecules or repeat units per 100 molecules or repeat units.

There are basically three different techniques that may be used to obtain lightly crosslinked matrices. One technique involves the use of a slightly greater number of diepoxide groups than phenolic groups (see earlier section on I.D. Catalyst and Reaction Conditions). When using this technique the repeat units will crosslink through the reaction of the secondary hydroxyl groups with the remaining epoxide groups. Once the polymer composition is prepared, it may be used alone or with a reinforcing fiber in an FRC-type (fiber reinforced composite) composition, wherein the polymer mass is heated to an elevated temperature (e.g. above 170° C.) and held at that temperature for the necessary time (typically about 2 to about 24 hours) to obtain crosslinking.

Another technique to obtain light crosslinking is to incorporate an appropriate amount of tri- or higher functional epoxide or tri- or higher functional phenolic or amine in the preparation of the polymer composition. The crosslinking agent, when added as a separate component, replaces a portion of the phenolic component or the epoxide component, as desired. For example, if 20% crosslinking agent is used, then 20% of the phenolic component is replaced on an equivalent basis.

Examples of suitable multifunctional epoxide polymers include Epon® Resin 1031 and Epon® Resin DPS-164 has the general formula

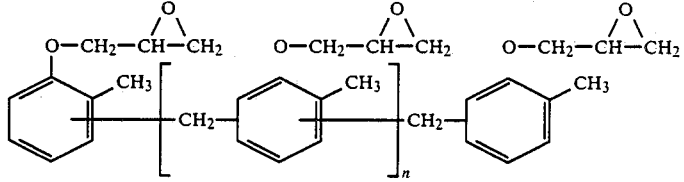

where n equals an average of 3.
Epon Resin 1031 has the structure

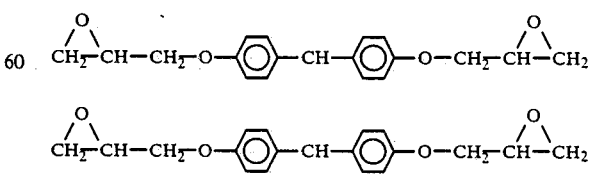

Other crosslinking agents include multifunctional amines such as EPON HPT™ *Curing Agents* 1061 and 1062, having the molecular structure:

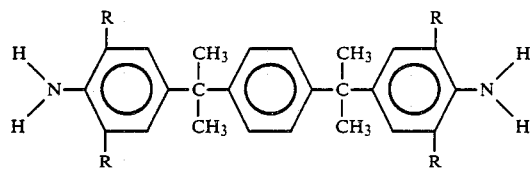

where R is H for CA 1061 and R is CH₃ for CA 1062. Still other crosslinking agents include

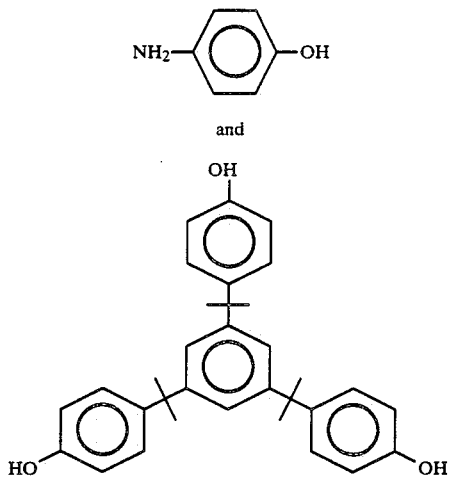

A third technique to obtain light crosslinking involves the addition of crosslinking agents, such as triepoxides, etc., to the resulting thermoplastic polymer. This technique is not preferred since it is more difficult to incorporate the crosslinking agent in the polymer after synthesis than before synthesis.

The amount of crosslinking agent chosen is selected to achieve the desired level of light crosslinking, as opposed to the normal crosslinking used for epoxy resins. Accordingly, when using a crosslinking agent such as EPON Resin 1031, the amount of equivalents used is 2 to 20%. Likewise, when the crosslinking agent is EPON HPT Curing Agent 1061, the amount of equivalents used is 5-50%.

C. Formulations and Composites

The composition optionally contains a reinforcing substrate. Suitable reinforcing materials include, for example, glass fibers, carbon fibers, Kevlar, boron, calcium carbonate, talc, alumina, asbestos and the like. The preferred fibrous reinforcing material for high-performance applications is selected from the group consisting of glass fibers, carbon fibers, boron fibers and Kevlar fibers, with continuous fiber being most preferred. The fibrous reinforcing material will be present in the composition in an amount effective to impart increased strength to the cured composition, generally from about 40 to about 95 weight percent, usually from about 60 to about 80 weight percent, based on the weight of the total composition.

The present composition can be applied to the fibrous reinforcing material from the melt or solution by methods known in the art. Among the various processes useful with the present invention include resin transfer molding (RTM), reaction injection molding (RIM), pultrusion, filament winding, sheet molding compound (SMC), and the use of prepregs. Such methods are known in the art, and are disclosed, for example, in the Handbook of Composites, Lubin, Ed., Van Nostrand Reinhold Company, 1982, pages 321-532, and in the book by Delmonte titled Technology of Carbon and Graphite Fiber Composites, Delmonte, Van Nostrand Reinhold Company, 1981.

One method of current interest involves the use of pre-pregs. In that syste, the polymer composition/curing agent—impregnated substrate, or "pre-preg", or a laminate prepared from a plurality of prepregs, is then cured. When the system is based on Epon ® RESIN 825 and BPA, the curing is typically accomplished at a temperature of about 150° to about 200° C. for about 1 to 10 hours under vacuum or under a presence of 1 atmosphere to 150 psi, to form the structural composite article.

D. Uses

The composition of the present invention have particular application in the automotive industry where the high impact performance obtainable with the present invention is required. In particular, RIM may be used to prepare large parts, such as underbodies. Pre-pregs may be used to prepare other auto parts. Filament winding may be used to prepare an entire assembly, while pultrusion may be used to prepare parts having a constant cross section.

The invention composition can optionally include additives for control or modification of various properties of the composition in its cured or uncured state, including cure rate accelerators or retardants, tackifiers and the like.

To illustrate the present invention, the following illustrative embodiments and comparative examples are given. It is to be understood, however, that the embodiments and examples are given for the purpose of illustration only and the invention is not to be regarded as limited to any of the specific materials or conditions used in the specific embodiments.

As used in the following examples, Epoxy Resin A is a liquid glycidyl polyether of 2,2-bis(4-hydroxyphenyl)-propane having an epoxide equivalent weight of 170-174 and an average molecular weight of about 345.

Epoxy Resin B is a liquid glycidyl polyether of 2,2-bis(4-hydroxyphenyl)propane having an epoxide equivalent weight of 180-195 and an average molecular weight of about 380.

The compositions were tested according to the following test procedures:

Flexural properties of neat resins were evaluated according to ASTM D790 method using 1/8 in. thick specimens. Specimens were tested both in Dry (at Room Temperature and ~75% R.H.) and Hot/Wet (after immersion in boiling water for 48 hours, test at 200° F., 5 min. equilibration time) conditions.

Fracture toughness, $K_q$, was measured using mini-compact tension specimens (see W. B. Jones, et al Am. Chem. Soc., Div. Polym. Chem., Polym. Prepr., 22, 1981). All specimens were slotted to a Chevron shape and then precracked with a razor blade.

Tensile properties were measured according to ASTM D638 method.

Swelling in solvents was evaluated by measuring weight gain per unit of initial weight after immersion in solvent for certain time periods at room temperature.

Illustrative Embodiment I

Polymerization of BPA and EPON 825 Resin

All of the materials used were recrystallized and thoroughly dried in a vacuum oven at 1 mm Hg vacuum before they were used.

In this example no separate crosslinking agent was used. Instead the phenol/epoxy ratio was 0.96. The components used were BPA and Epoxy Resin A.

The polymer of the present invention was made by melting the BPA and Epoxy Resin A together in the presence of a Na BPA catalyst at 180° C. in a vacuum erlenmeyer flask, degrassing the melt at 1 mm Hg until bubbling ceased, pouring the molten pre-polymer into a mold (made of two glass plates treated with a releasing agent preheated in a forced draft oven at 180° C.) and curing the polymer for 24 hours. At the end of the cure cycle, the polymer-in-mold was taken out of the oven and allowed to cool below its Tg and then the plates were popped loose.

The following properties were obtained:

$Tg = 115°$ C.

$K_q = 3600$ psi$\sqrt{in}$

Gel = 100%

Illustrative Embodiment II

In Illustrative Embodiment II various other polymers were prepared according to the invention. The various materials used were:

| Symbol | Chemical Name |
|--------|---------------|
| BP     | 4,4'-dihydroxybiphenyl |
| BPA    | 2,2-bis(4-hydroxyphenyl)propane |
| DGBPA  | 2,2-bis[4-(2,3-epoxypropoxy)phenyl]propane |
| BPFL   | 9,9-bis(4-hydroxyphenyl)fluorene |
| EOCN   | EPON Resin DPS-164 |

These polymers were prepared in a manner similar to that used in Illustrative Embodiment I. The results are shown below in Tables 1 and 1a. Run #1 is the same as that described in Illustrative Embodiment I.

TABLE 1

| Run # | Phenol Type, mole % | Epoxy Type | Crosslinking Agent Type | Crosslinking Agent Percent | P/E Molar ratio | Catalyst[1] Percent Theoretical | SU/FU | SU'/FU' | average # of stiff units divided by average # of flexible units |
|---|---|---|---|---|---|---|---|---|---|
| 1 | BPA, 100 | DGBPA | — | — | 0.96 | 75 | 2/0 | 2 | 2 |
| 2 | BPA, 80 BPFL, 20 | DGBPA | — | — | 0.96 | 75 | 2/1 5/0 | 2 | 2.57 |
| 3 | BPA, 40 BPFL, 60 | DGBPA | — | — | 0.96 | 75 | 2/1 5/0 | 2 | 4.17 |
| 5 | BP, 100 | DGBPA | — | — | 0.96 | 30 | 2/0 | 2 | 4 |
| 6 | BPA, 100 | DGBPA | EOCN | 5 | " | 100 | 2 | 2 | 2 |
| 7 | " | " | " | 20 | " | " | 2 | 2 | 2 |
| 8 | " | " | " | 30 | " | " | 2 | 2 | 2 |
| 9 | " | " | " | 50 | " | " | 2 | 2 | 2 |

[1]100% = 0.24% m basis epoxy.

TABLE 1a

| | | | Properties | | | | | | |
|---|---|---|---|---|---|---|---|---|---|
| Run # | Tg °C. | $K_q$ PSI | % Wt Gain (RT, Eq) | | | Flex Data (KSI) | | | Gel % |
| | | | MEK | CH$_2$Cl$_2$ | H$_2$O | E, dry | E, h/w | Stress | Strain ε | |
| 1 | 115 | 3600 | 65 | 123 | 2.5 | | | | | 100 |
| 2 | 128 | 3000 | | | | 396 | | 14.6 | >7 | |
| 3 | 153 | 2000 | | | | 375 | | 17.5 | 9 | |
| 5 | 128 | 4300 | | | | 280 | | 12 | >8 | |
| 6 | 121 | 2400 | | | | 370 | | 14.6 | 8 | |
| 7 | 130 | 1900 | | | | 390 | | 17.6 | 10 | |
| 8 | 143 | 1900 | | | | 410 | | 19 | 7 | |
| 9 | 169 | 600 | | | | 426 | | 20.5 | 8 | |

What is claimed is:

1. A polymer composition comprising lightly crosslinked linear molecules having the repeating structures prior to crosslinking of the general formula:

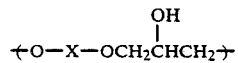

I.

and

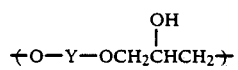

II.

wherein said repeating structures are lightly crosslinked such that between 1 and 50 of said repeating structures per 100 total repeating structures are crosslinked to repeating structures of other molecules, and where:
(a) "X" represents a segment comprising stiff units (SU) and optional flexible units (FU), which stiff units and flexible units are interconnected;
(b) "Y" represents a segment comprising stiff units (SU') and optional flexible units (FU') which stiff units and flexible units are interconnected;
(c) said stiff units, SU and SU', are independently selected from the group consisting of substituted and non-substituted aromatic rings and non-interferring heterocyclic rings;
(d) said flexible units, FU and FU', are independently selected from the group consisting of

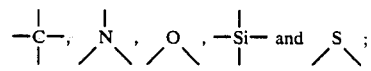

(e) the number of X segments in said molecules is "a", the number of y segments in said molecules is "b", the number of stiff units and flexible units is selected such that the average number of total stiff units $$\left(\left(\frac{a}{a+b}\right) \cdot SU + \left(\frac{b}{a+b}\right) \cdot SU'\right)$$

divided by the average number of total flexible units $$\left(\left(\frac{a}{a+b}\right) \cdot FU + \left(\frac{b}{a+b}\right) \cdot FU'\right)$$

is less than or equal to four; and (f) the ratio of the number of stiff units to flexible units in said X segment (SU/FU) is equal to or greater than the ratio of the number of stiff units to flexible units in said y segment (SU'/FU').

2. The composition of claim 1 wherein the average number of total stiff units divided by the average number of total flexible units is greater than 1.5 and less than 4.

3. The composition of claim 2 wherein the average number of total siff units divided by the average number of total flexible units is about 2.

4. The composition of claim 1 wherein said stiff units are non-substituted aromatic rings.

5. The composition of claim 4 wherein said flexible units are

6. The composition of claim 1 wherein the ratio of $$\frac{SU}{FU} > \frac{SU'}{FU'} + 0.5.$$

7. The composition of claim 1 wherein said repeating structures are lightly crosslinked such that between 1 and about 20 repeating structures from different molecules per 100 of said repeating structures are crosslinked together.

8. The composition of claim 7 wherein between 3 and 10 per 100 repeating structures are crosslinked together.

9. The composition of claim 1 which further comprises a crosslinking agent.

10. The composition of claim 9 wherein an effective amount of crosslinking agent is employed such that between about 1 and about 50 repeating structures from different molecules per 100 of said repeating structures are crosslinked together during cure.

11. The composition of claim 7 which further comprises a fibrous reinforcing material.

12. The composition of claim 10 which further comprises a fibrous reinforcing material.

13. The composition of claim 11 wherein the fibrous reinforcing material is selected from the group consisting of glass fibers, carbon fibers, boron fibers and Kevlar fibers.

14. The composition of claim 12 wherein the fibrous reinforcing material is selected from the group consisting of glass fibers, carbon fibers, boron fibers and Kevlar fibers.

15. The cured composition of claim 14 having a glass transition temperature up to about 150° C.

16. A prepreg comprising the composition of claim 10 and a fibrous reinforcing material.

17. A prepreg comprising the composition of claim 14.

18. An article of manufacture prepared from the prepreg of claim 16.

19. The composition of claim 1 having a glass transition temperature up to about 150° C., a flex modulus of at least 250 KSI and a fracture toughness of at least 1000 psi$\sqrt{in}$.

20. The composition of claim 9 wherein the crosslinking agent is selected from the group consisting of tri- or higher functional epoxides, tri- or higher functional phenolics, tri- or higher functional amines or mixtures thereof.

21. The composition of claim 1 wherein said linear molecules are prepared by the process comprising reacting:

(a) a first component selected from the group consisting of phenol compounds of the formula HO—X—OH and HO—Y—OH;

(b) a second component selected from the group consisting of diepoxide compounds of the structures:

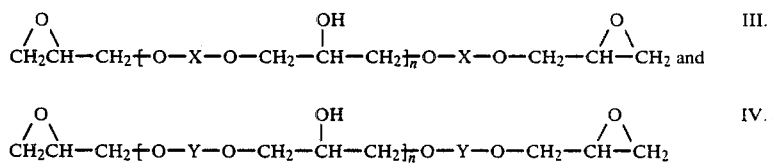

and wherein n is 0 to 6

(c) a catalytic amount of a basic condensation catalyst at an elevated temperature and with a molar ratio of phenol compounds to diepoxides of about 0.90 to about 1.04 until the desired linear reaction product has been formed, and thereafter stopping the reaction.

22. The composition of claim 21 wherein said first and second components are reacted together in the presence of an effective amount of a crosslinking agent.

23. The compositions of claim 22 wherein the crosslinking agent is selected from the group consisting of tri- or higher functional epoxides, tri- or higher functional phenolics, tri- or higher functional amines or mixtures thereof.

24. The composition of claim 23 wherein the amount of crosslinking agent employed is such that between about 1 and about 50 repeating structures from different molecules per 100 of said repeating structures are crosslinked together during cure.

25. The composition of claim 21 wherein the amount of catalyst employed is not in excess of 0.1 mole per mole of said first component.

26. The composition of claim 21 wherein said first and second components are reacted at a temperature of about 130° C. to about 230° C. for about 1 to about 24 hours.

27. The composition of claim 21 wherein said first component is BPA and said second component is the diglycidyl ether of BPA.

28. The composition of claim 1 wherein X is

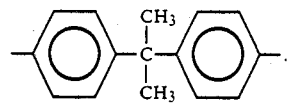

29. The composition of claim 28 wherein Y is

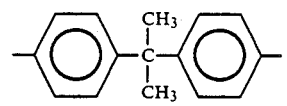

* * * * *